(12) United States Patent
Chen et al.

(10) Patent No.: US 6,896,519 B2
(45) Date of Patent: May 24, 2005

(54) METHOD OF ORAL TRANSMUCOSAL DELIVERY OF A THERAPEUTIC AGENT

(75) Inventors: Lingjun Chen, Brookline, MA (US); Shuqi Chen, Brookline, MA (US)

(73) Assignee: Chen & Chen, LLC, Framingham, MA (US)

( * ) Notice: Subject to any disclaimer, the term of this patent is extended or adjusted under 35 U.S.C. 154(b) by 180 days.

(21) Appl. No.: 10/229,365

(22) Filed: Aug. 27, 2002

(65) Prior Publication Data

US 2003/0075731 A1 Apr. 24, 2003

Related U.S. Application Data

(63) Continuation-in-part of application No. 09/744,138, filed as application No. PCT/US99/16256 on Jul. 23, 1999, now Pat. No. 6,439,889.
(60) Provisional application No. 60/094,316, filed on Jul. 27, 1998.

(51) Int. Cl.[7] .................................................. A61C 5/00
(52) U.S. Cl. ...................................................... 433/215
(58) Field of Search ........................ 433/216, 93, 168.1, 433/214, 6, 71, 80, 215; 601/139, 164; 128/859; 604/514, 77

(56) References Cited

U.S. PATENT DOCUMENTS

| | | | |
|---|---|---|---|
| 2,957,476 A | 10/1960 | Freeman | 128/229 |
| 3,686,761 A | 8/1972 | Gravon | 32/19 |
| 3,742,942 A | 7/1973 | Westline | 128/62 A |
| 4,059,101 A | 11/1977 | Richmond | 128/62 A |
| 4,148,309 A * | 4/1979 | Reibel | 601/2 |
| 4,164,940 A | 8/1979 | Quinby | 128/62 A |
| 4,624,640 A | 11/1986 | Tesini | 433/71 |
| 5,104,315 A | 4/1992 | McKinley | 433/80 |
| 5,235,991 A | 8/1993 | Minneman | 128/859 |
| 5,346,395 A | 9/1994 | Adell | 433/71 |
| 5,455,285 A | 10/1995 | Carroll | 523/109 |
| 5,503,552 A | 4/1996 | Diesso | 433/37 |
| 5,503,629 A * | 4/1996 | Catone et al. | 604/77 |
| 5,575,655 A * | 11/1996 | Darnell | 433/216 |
| 5,800,167 A | 9/1998 | Adell | 433/71 |
| 5,980,249 A * | 11/1999 | Fontenot | 433/80 |
| 6,386,869 B1 * | 5/2002 | Zegarelli | 433/80 |
| 6,439,889 B1 | 8/2002 | Chen et al. | 433/216 |
| 2002/0110780 A1 | 8/2002 | Zegarelli | 433/80 |
| 2003/0211440 A1 | 11/2003 | Kuo et al. | 433/6 |

FOREIGN PATENT DOCUMENTS

| | | |
|---|---|---|
| FR | 2 630 905 | 11/1989 |
| WO | WO 00/06045 | 2/2000 |
| WO | WO 02/24100 | 3/2002 |

OTHER PUBLICATIONS

European Search Report for EP 99938757 4, mailed Dec. 8, 2004.

* cited by examiner

*Primary Examiner*—Todd E. Manahan
(74) *Attorney, Agent, or Firm*—Foley Hoag LLP; Scott E. Kamholz

(57) ABSTRACT

A mouthpad for cleaning teeth and oral transmucosal drug delivery has a U-shaped plate sized to cover substantially only the biting surfaces of upper and lower teeth of a human jaw. The plate is positioned between the upper teeth and lower teeth such that when the teeth are rinsed with a liquid, the liquid flows primarily through the crevices between individual teeth and physically detaches the adhering residue within. Alternatively, using fluids containing drugs for rinsing while biting on the plate can deliver drugs through the oral mucosa. A method of cleaning teeth and delivering drugs through oral mucosa using a plate positioned between the upper and lower teeth is also disclosed.

21 Claims, 3 Drawing Sheets

METHOD OF ORAL TRANSMUCOSAL DELIVERY OF A THERAPEUTIC AGENT

CROSS-REFERENCE TO RELATED APPLICATIONS

The present application is a continuation-in-part of U.S. patent application Ser. No. 09/744,138, filed Jan. 19, 2001 now U.S. Pat. No. 6,439,889, which is the U.S. National Stage Application of International PCT Application No. PCT/US99/16256 filed Jul. 23, 1999, which claims priority to U.S. Provisional Patent Application No. 60/094,316, filed Jul. 27, 1998. Each of the aforementioned patent applications is incorporated herein by reference.

INTRODUCTION

The present invention is directed to an apparatus for teeth cleaning and oral delivery of an agent, more particularly, to a teeth cleaning apparatus which can efficiently clean crevices between the teeth and deliver agents, such as a therapeutic or cosmetic agent, orally.

BACKGROUND

Conventional dental cleaning methods have many limitations and disadvantages. Brushing the teeth can only clean the tooth surfaces that a brush can reach. Therefore, brushing cleans only the exposed surfaces of teeth, not the crevices between teeth. Flossing can reach most of these crevices, but it is inconvenient to use, particularly for children. Since plaque formation occurs after meals and its adhesion to teeth is enhanced with time, the plaque is much more easily removed immediately after meals. Because of the inconveniences of flossing, people rarely floss after each meal. As time goes by, the plaque becomes hard to remove. Rinsing teeth with mouthwash is convenient enough to be done immediately after meals. However, rinsing does not clean the crevices between teeth very well. When the jaw is closed, open spaces are typically formed between the upper and lower teeth. These spaces are much larger than the crevices between adjacent teeth. The larger spaces provide a shortcut for the mouthwash to bypass the crevices. Thus, when rinsing, most of the mouthwash or water flows through the larger open spaces between the upper teeth and the lower teeth, and only a very small amount of mouthwash may flow through the crevices. Not only is the amount of mouthwash flowing through the crevices reduced, the pressure applied on the crevices is also diminished due to the bypass of mouthwash through the open spaces, resulting in a lower flow rate in the crevices. Such a low flow rate of a small amount of mouthwash has insufficient wash power to clean the narrow crevices between the teeth. Hence, even if the mouthwash can kill bacteria, rinsing with mouthwash can hardly wash out the attached dead bacteria, plaque and other adhering residues on the tooth surfaces in the crevices. These remaining residues still provide bacterium with a breeding ground. Therefore, rinsing with mouthwash cannot effectively clean the narrow crevices between teeth. These narrow crevices are inhabited by plaque and other bacteria, which cause bad breath, tooth decay and cavities. Currently, there is no efficient and convenient way to clean them.

The oral mucosa is an attractive and feasible site for systematic and localized drug delivery due to its relative permeability, its high concentration of blood vessels, short recovery time after damage, tolerance to allergens, and acceptability to patients. Furthermore, oral transmucosal drug delivery bypasses first pass effects and avoids presystematic elimination in the gastrointestinal tract. Current methods of transmucosal drug delivery requires drug containing gels or films to be injected or implanted under the gum line or in mucosal tissue. Such procedures must be performed by trained dental physician in a clinical setting. These gels or films are designed to facilitate the sustained release of drugs over a limited time frame. Thus patients are required to return to the clinic periodically and have the expired gel or film removed and a new gel or film implanted. These treatments are expensive, uncomfortable and inconvenient for patients.

It is an object of the present invention to provide an apparatus for teeth crevice cleaning and for delivering an agent orally which reduces or overcomes some or all of the aforesaid difficulties inherent in prior known devices. Particular objects and advantages of the invention will be apparent to those skilled in the art, that is, those who are knowledgeable or experienced in this field of technology, in view of the following disclosure of the invention and detailed description of certain preferred embodiments.

SUMMARY

The principle of the invention combines the convenience of rinsing with the function of flossing to create an easy-to-use, convenient and efficient dental care product. An apparatus is used to block the spaces between the upper teeth and the lower teeth during occlusion, that is, when the biting surfaces of the upper teeth and the lower teeth are brought together. In use, the apparatus does not cover or block the crevices between adjacent teeth. Thus, when rinsing, the mouthwash is forced to flow through the crevices between the teeth rather than the spaces between the upper teeth and the lower teeth. This generates a high shear force, or wash power, that is applied on the tooth surfaces and washes away the residues in the crevices and under the gum line to prevent plaque from forming.

The present invention may also be used as a mechanism for oral delivery of an agent such as a therapeutic agent. For example, when rinsing with an agent, such as a therapeutic agent, the apparatus of the present invention may drive a liquid stream containing an agent under the gum line to deliver the agent transmucosally.

In accordance with a first aspect, an apparatus for cleaning teeth has a U-shaped plate sized to cover substantially only the biting surfaces of upper and lower teeth of a human jaw. In accordance with another aspect, a kit may comprise a U-shaped plate sized to cover substantially only the biting surfaces of upper and lower teeth of a human jaw and a liquid mouthwash or a therapeutic agent.

In accordance with another aspect, a mouthpad for facilitating cleaning of crevices between adjacent teeth, the mouthpad comprising a U-shaped plate sized and shaped to cover substantially biting surfaces of upper teeth and lower teeth of a human jaw and thereby substantially block spaces between the upper teeth and the lower teeth during occlusion, while leaving substantially unobstructed the crevices between adjacent upper teeth and the crevices between adjacent lower teeth.

In accordance with another aspect, a method of delivering liquid into the mouth of a user comprises inserting a U-shaped plate sized to cover substantially only the biting surfaces of upper and lower teeth of a human jaw into a mouth of a user; drawing an appropriate amount of liquid into the mouth; biting down on the plate; rinsing the liquid while biting down on the plate; and removing the liquid and the plate from the mouth.

In accordance with yet another aspect, an apparatus for delivering drugs comprising a U-shaped plate sized to cover substantially only the biting surfaces of upper and lower teeth of a human jaw; and at least one therapeutic agent or cosmetic agent.

In accordance with yet another aspect, a method comprises inserting a U-shaped plate sized to cover substantially only the biting surfaces of upper and lower teeth of a human jaw into a mouth of a user; biting down on the plate; stimulating and accumulating saliva; rinsing with the saliva repeatedly while biting down on the plate; and removing the plate from the mouth.

In accordance with yet another aspect, a method of oral transmucosal delivery of a therapeutic agent comprises inserting a U-shaped plate containing at least a therapeutic agent into a mouth of a user; drawing liquid into the mouth of a user; rinsing with the liquid while biting down on the plate; and removing the plate and liquid from the mouth.

In accordance with yet another aspect, a method of oral transmucosal delivery of a therapeutic agent comprises inserting a U-shaped plate into a mouth of a user; drawing liquid containing a therapeutic agent into the mouth of a user; rinsing with the liquid while biting down on the plate; and removing the plate and liquid from the mouth.

From the foregoing disclosure, it will be readily apparent to those skilled in the art that the present invention provides a significant technological advance. Preferred embodiments of the present invention can provide increased efficiency, convenience and comfort in cleaning the crevices between adjacent teeth. These and additional features and advantages of the invention disclosed here will be further understood from the following detailed disclosure of certain preferred embodiments.

BRIEF DESCRIPTION OF THE DRAWINGS

Certain preferred embodiments are described in detail below with reference to the appended drawings wherein.

Figure 1:
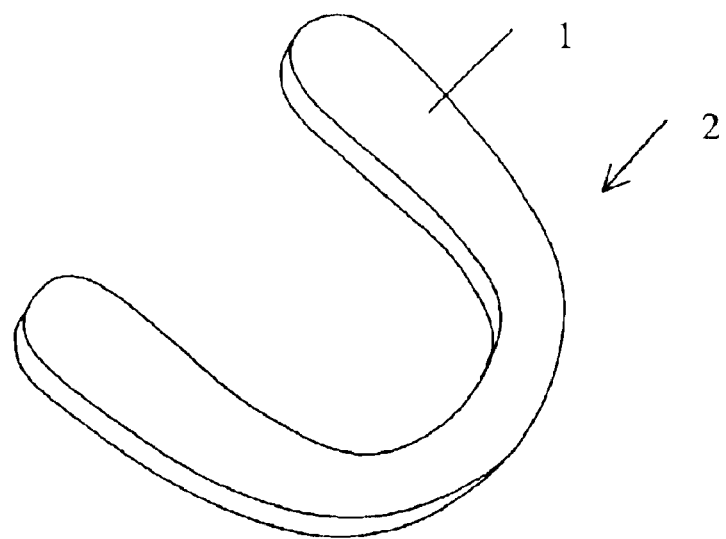
FIG. 1 is a schematic perspective view of a preferred embodiment of the teeth crevice cleaning apparatus of the present invention.

The figures referenced above are not drawn necessarily to scale and should be understood to present a representation of the invention, illustrative of the principles involved. Some features of the teeth crevice cleaning apparatus depicted in the drawings have been enlarged or distorted relative to others to facilitate explanation and understanding. The same reference numbers are used in the drawings for similar or identical components and features shown in various alternative embodiments. Teeth crevice cleaning apparatus as disclosed herein, will have configurations and components determined, in part, by the intended application and environment in which they are used.

DETAILED DESCRIPTION OF CERTAIN PREFERRED EMBODIMENTS

Figure 2:
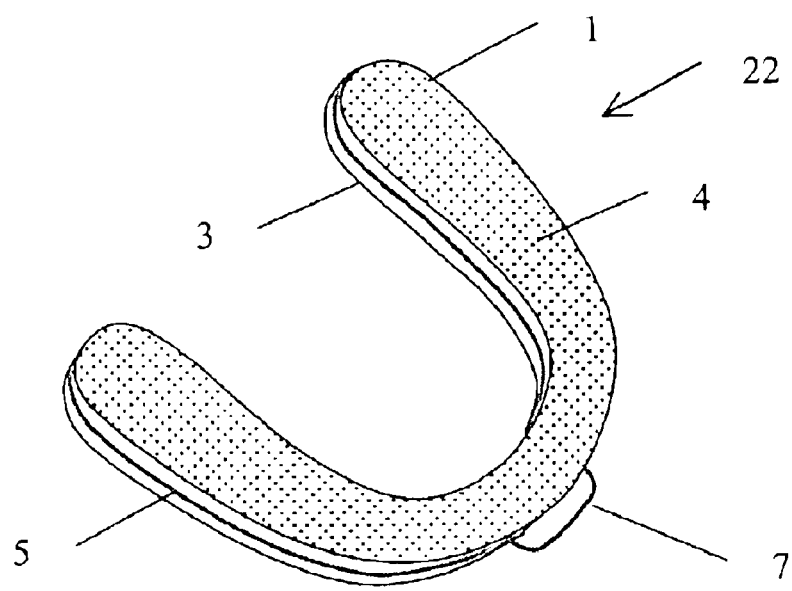
FIG. 2 is a schematic perspective view of an alternative embodiment of the teeth crevice cleaning apparatus of the present invention.

Referring to FIG. 1, a mouthpad according to the present invention is shown generally by the reference numeral 2. Mouthpad, as used herein, refers to a device or apparatus which is inserted into the mouth of a user and is positioned between the user's upper and lower teeth to aid in cleaning crevices between adjacent teeth or to aid in the oral delivery of an agent. Mouthpad 2 comprises a plate 1 having a U-shape. In certain preferred embodiments, plate 1 is made of a resilient, foam-like material, such as a polymer or other suitable materials. The U-shape of mouthpad 2 substantially matches a human jaw to cover substantially only the interfaces of all the teeth during occlusion, that is, when the biting surfaces of the upper and lower teeth are brought together. Thus, mouthpad 2 covers substantially only the biting surfaces of the teeth, leaving the crevices between adjacent teeth on the front and back of the teeth substantially unobstructed. Mouthpad 2 is sized to fit in between the upper teeth and the lower teeth during occlusion, and is preferably approximately 2 mm to 12 mm thick, most preferably approximately 5 mm to 8 mm thick. Thus, mouthpad 2 provides the function of blocking the spaces between the upper teeth and the lower teeth during occlusion. When rinsing with mouthpad 2, mouthwash or other liquid held in the mouth is advantageously forced to flow through the crevices between individual teeth rather than through the spaces between the upper teeth and the lower teeth. This generates a great shear force that is applied on the tooth surfaces and washes away any residue in the crevices to prevent plaque from forming. In certain preferred embodiments, mouthpad 2 can be disposable, while in other embodiments, mouthpad 2 may be reused. Another preferred embodiment is shown in FIG. 2. In this embodiment, plate 1 of mouthpad 22 has a sandwich structure formed of a top layer 4, a bottom layer 3, and a central layer 5 disposed between top and bottom layers 4, 3. Top and bottom layers 4, 3 are preferably made of a resilient, foam-like material, such as a polymer or other suitable material. Top and bottom layers 4, 3 are preferably approximately 2 mm to 6 mm thick and are attached respectively on each side of the central layer 5 by gluing, molding or other suitable means. Central layer 5 is a thin sheet of material capable of being easily shaped. Central layer 5 may be formed of a suitable malleable or ductile material, such as copper or cellulose, with a thickness of approximately 0.05 to 1 mm, depending on the material used. Central layer 5 functions as the skeleton of mouthpad 22. When a user bites down on mouthpad 22 for the first time, their teeth mold central layer 5 so that mouthpad 22 matches the profile of a user's teeth.

In certain preferred embodiments, as illustrated in FIG. 2, a handle 7 can be attached to mouthpad 22 in order to facilitate insertion and removal from the mouth. Handle 7 can be formed of any suitable material including, for example, plastic or foam.

Figure 3:
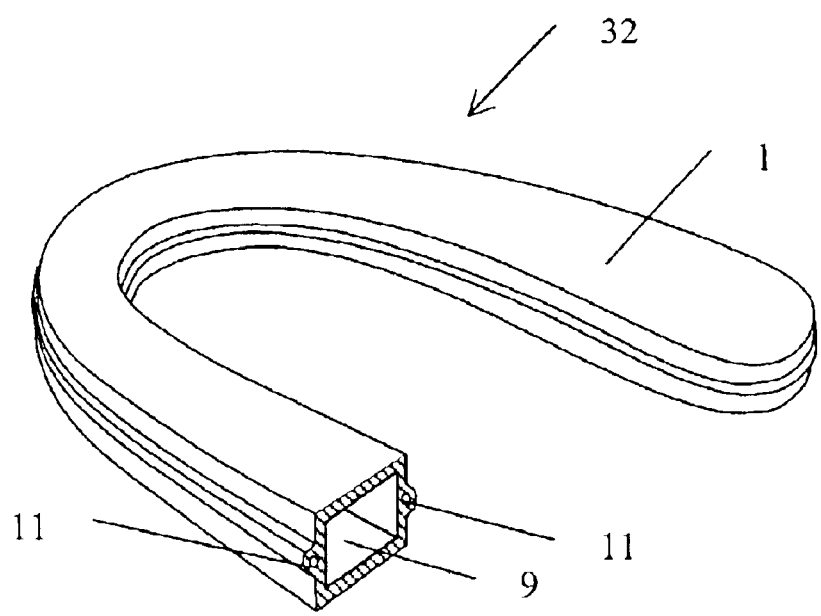
FIG. 3 is a schematic perspective view, shown partially in section, of another alternative embodiment of the teeth crevice cleaning apparatus of the present invention.

Another preferred embodiment is shown in FIG. 3, where mouthpad 32 contains a pocket 9. Pocket 9 typically contains air at ambient pressure, but may, in other preferred embodiments, contain other gases or fluids at any desired pressure. Mouthpad 32 is preferably formed of a resilient rubber-like material, such as, for example, polyvinyl chloride (PVC), nylon, or silicon rubber. Other suitable materials for mouthpad 32 will become readily apparent to those skilled in the art, given the benefit of this disclosure. In certain preferred embodiments, a stiffening member 11 is secured within mouthpad 32 adjacent its outer periphery.

Stiffening member 11 serves as the skeleton of mouthpad 32 to conform mouthpad 32 to a desired shape. Stiffening member 11 may be formed of wire or other suitable material. When a user bites down on mouthpad 32, the upper teeth and the lower teeth compress the air inside air pocket 9. As a result, the air pressure forces the resilient material of mouthpad 32 to conform to the shape of the users teeth, forming balloons which block the irregular spaces formed by, for example, misaligned or missing teeth.

Figure 4:
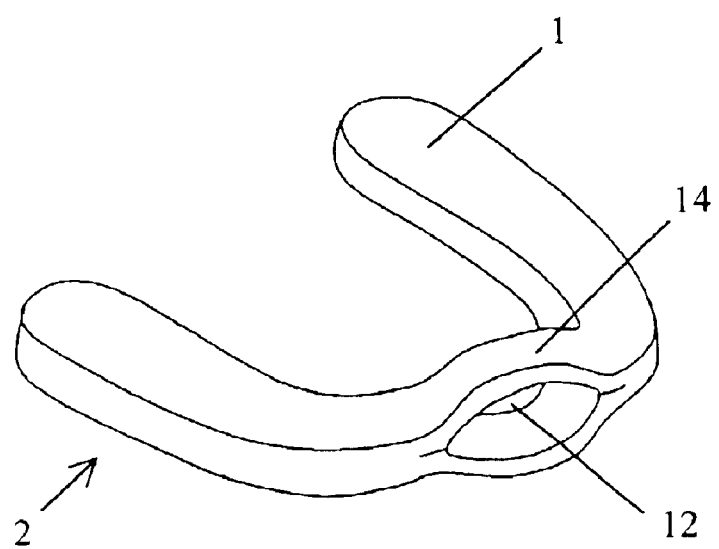
FIG. 4 is a schematic perspective view of another alternative embodiment of the teeth crevice cleaning apparatus of FIG. 1, shown with an aperture through said device.

In certain preferred embodiments, the plate 1 has an aperture 12 through the forward portion of plate 1 at the base of the U-shape, as shown in FIG. 4. Aperture 12 provides a channel to bring liquids, such as mouthwash, into the mouth from a container (not shown). The aperture may be centrally located on the plate, as illustrated, or may be positioned at other locations on the plate. The aperture 12 may be sized and shaped to facilitate the flow of a desired volume of liquid through the plate. The aperture allows a user to draw liquid into his/her mouth while the mouthpad is 2 is positioned within the jaw of the user. Thus, a user may insert and properly align mouthpad 2 before drawing liquid into his/her mouth through the aperture 12. In certain embodiments, the section 14 of the plate 1 that forms the aperture 12 may be formed of a resilient, elastic material to facilitate selective opening and closing of the aperture 12 by the user. For example, when compressed by the jaw, section 14 may be compressed and closed off to stop liquid flow through aperture 12. When released by the jaw, section 14 may restore the aperture 12 to the initial open configuration to allow liquid to be expectorated through aperture 12.

Figure 5:
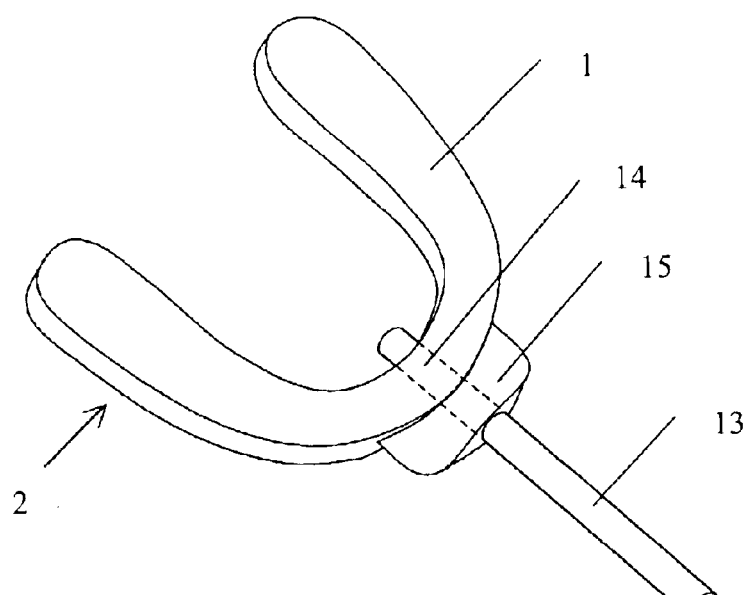
FIG. 5 is a schematic perspective view of another alternative embodiment of the teeth crevice cleaning apparatus of FIG. 1, shown with a suction tube; and, FIG. 6 is a schematic plan view of a measurement card suitable for use in conjunction with the teeth crevice cleaning apparatus of FIG. 1.

In certain preferred embodiments, a suction tube 13 can extend through aperture 12 of plate 1, as seen in FIG. 5. Tube 13 provides a channel to bring liquid into the mouth from a container (not shown). A shoulder 15 may be attached to the front of plate 1, having tube 13 extending therethrough. Shoulder 15 may be formed of the same material as plate 1, or any other suitable material. Shoulder 15 is shaped to provide a smooth interface with the lips of a user to prevent leakage.

In certain preferred embodiments, the mouthpad can be coated with or otherwise contain an antiseptic substance and/or other substance such as flavoring. For example, the mouthpad can be soaked with an antiseptic liquid, such as mouthwash.

In certain preferred embodiments, the U-shaped plate 1 may include particles capable of detaching from the U-shaped plate and dissolving in a liquid over time. Suitable particles may be approximately 1 $\mu$m to 500 $\mu$m in diameter, and, in certain embodiments, may be approximately 100 $\mu$m to 200 $\mu$m in diameter. The size of particles may be selected based on the size of the gaps between adjacent teeth of the user and the desired dissolve rate of the particles. For example, larger particles may be selected to clean larger gaps between adjacent teeth or to provide a longer dissolve rate. The particles can be made of polysaccharides, other biodegradable and water-soluble polymers, polymer microspheres or capsules, gels or other materials that may dissolve within a liquid and may be suitable for use orally. Particles can be coated on to the mouthpad in dry form. Alternatively, particles can be mediated in liquid suspension and then be absorbed in, immobilized on, sprayed or coated on the mouthpad. When the mouthpad is placed inside of a mouth and submerged in a liquid, such as water, mouthwash or saliva, the particles may detach from the plate to form a particle suspension. When rinsing with this particle suspension, the particles may flow with the liquid through the teeth crevices and under the gum line and scrub the tooth surface to physically remove residues. Particles that remain in the gaps between teeth, the gums or "pockets" after rinsing may dissolve in a liquid, such as saliva, in a short time period, preferably in the order of minutes to hours. In other embodiments, the particles can be contained in a liquid to be used for rinsing.

In certain preferred embodiments, the mouth pad can be coated with, may absorb, may be soaked in, packed with or otherwise contain an agent in liquid or solid form, or in particle form as disclosed above. The agent may be a therapeutically or pharmaceutically active agent, i.e., an agent that is administered for the purpose of treatment of a subject. The agent may be an agent for curing, improving at least one symptom of a disease or condition or for preventing the occurrence of a disease or condition. The disease or condition may be one relating to the mouth, e.g., gums, tongue, throat, or teeth of a subject. Alternatively, the disease or condition may be one relating to other parts of the body of a subject, such as an organ or tissue, e.g., heart, lungs, liver, spleen, glands, skin, immune system, brain, bone, cartilage, mesenchymal tissue, or epithelial tissue. Exemplary diseases or conditions include inflammatory conditions, e.g., a gum or teeth infection; a malignant (e.g., cancer) or non-malignant tumor; and infections by microorganisms, such as viral and bacterial infections. A person of skill in the art will recognize that a subject can be a mammal, such as a human, a bovine, ovine, porcine, canine or feline.

The agent may also be a cosmetic agent such as bleach or other compositions for effecting whitening of teeth.

The agent may be of any type of molecule or complexes of molecules. For example, an agent may be a small organic molecule, a chemical compound, a protein, a peptide, a nucleic acid (such as DNA or RNA), a polysaccharide, a lipid, or any combination thereof. The agent may be an agent that acts outside of cells, such as outside of cells in a tissue or outside of cells and tissues, e.g., in the mouth. Exemplary agents include those that bind to specific or non-specific receptors on the cell surface; agents that affect the conditions outside the cell, such as the pH of the saliva; agents that coat teeth, e.g., with a protective layer; agents that kill or effect extracellular microorganisms, such as viruses and bacteria. The agent may also be an agent that acts inside of cells, such as cells in a tissue.

Exemplary agents include antibiotics, such as doxycycline and monocycline; hormones, such as insulin; isosorbide dinitrate; lignocaine; selegiline; anesthetic drugs; fluoride; and other agents known to those skilled in the art.

In certain embodiments, an agent is further complexed with or administered together with a second agent, e.g., an agent that facilitates penetration of the first agent (e.g., a therapeutic agent) into a tissue, into cells, into the blood stream or across the blood-brain barrier. In one embodiment, an agent is provided together with a permeation enhancer, such as bile salts, fatty acid esters, such as laureate, myristate and stearate monoesters of polyethylene glycol, enamine derivatives and alpha-keto aldehydes; sodium cholate; sodium glycocholate; sodium deoxycholate; sodium lauryl sulfate; sodium salicylate; sodium ethylenediaminetetraacetc acid (EDTA); aprotinin; azone; sodium 5-methoxysalicylate; 1-oleylazacycloheptan-2-one; and other substances known to those skilled in the art.

Exemplary agents enhancing uptake of a particular agent into cells include lipids or complexes of lipids or comprising lipids, e.g., liposomes. Liposomes are, e.g., hollow spherical vesicles composed of lipids arranged in a similar fashion as those lipids which make up the cell membrane. They may have an internal aqueous space for entrapping water soluble compounds and range in size from 0.05 to several microns in diameter. For example, a liposome delivery vehicle originally designed as a research tool, Lipofectin, has been shown to deliver intact molecules to cells. Liposomes offer several advantages: They are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system. Lipid aggregates can be formed with macromolecules using, e.g., cationic lipids alone or including other lipids and amphiphiles such as phosphatidylethanolamine. Liposomes comprising cationic lipids are favored for delivery of negatively charged molecules.

Other drug delivery vehicles that can be used include hydrogels, cyclodextrins, biodegradable polymers (surgical implants or nanocapsules), and bioadhesive microspheres.

Agents may also be provided together with a sustained release mechanism, which may include, e.g., polymer microspheres, and other mechanisms known to those skilled in the art to vary the rate of release of an agent. Accordingly an agent, such as a therapeutic agent may be provided together with at least one permeation or permeability enhancer, and/or optionally, may comprise at least one sustained release mechanism.

In another preferred embodiment, the mouthpad is formed of chewing gum material. Conventional chewing gum can easily be formed into the desired U-shaped mouthpad. The plasticity of the gum provides the function of blocking the spaces between the upper teeth and the lower teeth. The mouthpad can then be chewed in conventional manner after it is used to clean teeth.

Figure 6:
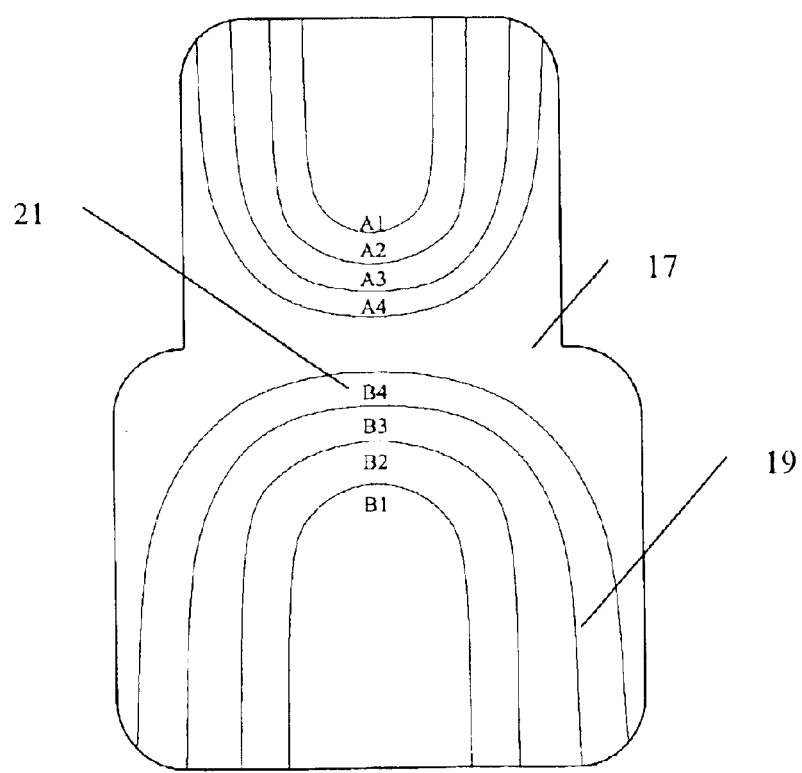

To fit different jaw sizes, different sized mouthpads are needed. As seen in FIG. 6, a measurement card 17 is designed for selecting a suitable sized mouthpad. Such cards are disposable and made of a sheet of soft material easily accepting teeth marks. Suitable materials include, for example, cardboard, plastic, and Styrofoam®. Measurement card 17 is marked with size indicating lines 19 which are labeled by size marks 21 which reference the different sizes for mouthpads. In a preferred embodiment, a booklet of measurement cards 17 is made available next to the mouthpads in a store for a customer to use in selecting a suitably sized mouthpad.

In another preferred embodiment, the mouthpad may be formed of gelatin-like material with a self-hardening function. A piece of such material is put into the individual's mouth and positioned between the upper and lower teeth covering the biting surfaces of the teeth. The individual then bites down on the piece of material for a certain amount of time to form a customized jaw shaped pad, which has the individual's teeth prints embedded in it. After being removed from the mouth, the stiffened pad can be modified, if necessary, into a mouthpad, or can be made into a mouthpad according to the shape of the jaw. Thus, such a mouthpad is customized to the individual's teeth contour and jaw size.

A kit according to the present invention comprises mouthpad 2 and a liquid for rinsing the teeth crevices. The liquid may be, for example, mouthwash specifically designed for rinsing teeth. The liquid may contain a detergent to enhance the cleaning performance. Plate 1 of the kit may, in certain preferred embodiments, include tube 13 and shoulder 15, and/or handle 7.

A kit according to the present invention may comprise a mouthpad 2 and a liquid containing an agent, such as one or more of the agents described above. Alternatively, the kit may comprise a mouthpad 2 that is coated with an agent, or otherwise contains an agent in a dried state or inactive state, and a liquid containing an activator for activating the agent. The activator may be, for example, a catalyst, a composition that facilitates the agent dissolving in the liquid or releasing the agent from the mouthpad 2, or a composition that renders the agent to an active state. The kit may also include one or more additional agents, such as a permeation enhancer and/or a sustained release mechanism.

When using the apparatus of the present invention, a user first puts the mouthpad into their mouth and then draws mouthwash or other liquid into the mouth. Alternatively, the mouthwash or other liquid may be drawn into the mouth before the mouthpad is inserted into the mouth. In certain preferred embodiments, the liquid can be drawn into the mouth through aperture at the front portion of the mouthpad or through a suction tube. After an appropriate amount of liquid enters the mouth, the user bites down on the mouthpad to block the spaces between the upper teeth and the lower teeth. In embodiments using a suction tube, biting down on the mouthpad also closes off the suction tube. The user then rinses in conventional manner, by pushing the liquid from the oral cavity, that is, between the rear of the teeth and the pharynx, to the buccal cavity, that is, between the lips and cheeks and the front of the teeth and then, vice versa. Since the mouthpad is substantially blocking the larger spaces between the upper teeth and the lower teeth, most of the mouthwash is forced to flow though the crevices between the teeth. This generates great shear forces that detach and wash away residues that adhere to the hard-to-reach surfaces, thus cleaning the crevices between teeth. When rinsing, the occluded teeth act as a filter and catch anything too large to pass through the crevices between teeth. To remove the caught residues, the liquid may be spat out on each side of the teeth respectively. After rinsing for a sufficient time, the user spits out the liquid from one side of the teeth. Additional liquid may then be drawn into the mouth for a second rinsing, after which the user spits out the liquid from the other side of the teeth. The mouthpad is then removed from the mouth. In embodiments where the mouthpad is formed of chewing gum, the mouthpad is chewed rather than removed from the mouth.

In embodiments employing an agent, such as a therapeutic agent, rinsing in the manner described above can deliver the agent orally to the teeth, to transmucosal tissue, or to other surfaces within the mouth.

To select a suitable mouthpad, a user places a measurement card in their mouth and bites down on the card to make teeth marks. After taking the card out of their mouth, the user can compare the location of teeth marks to the size lines on the card to determine the appropriate size mouthpad for that user's teeth.

In light of the foregoing disclosure of the invention and description of the preferred embodiments, those skilled in this area of technology will readily understand that various modifications and adaptations can be made without departing from the true scope and spirit of the invention. All such modifications and adaptations are intended to be covered by the following claims.

We claim:

1. A method of oral transmucosal delivery of a therapeutic agent comprising:
   inserting a U-shaped plate sized to covet substantially only the biting surfaces of upper and lower teeth of a human jaw into a mouth of a user, the plate comprising at least a therapeutic agent;
   drawing liquid into the mouth of a user;
   rinsing with the liquid while biting down on the plate; and
   removing the plate and liquid from the mouth.

2. The method according to claim 1, wherein the liquid includes an activator for the therapeutic agent.

3. The method according to claim 1, further comprising repeatedly rinsing the liquid while biting down on the plate.

4. The method according to claim 1, wherein the plate is formed of resilient material.

5. The method according to claim 1, wherein the therapeutic agent comprises at least one of an antibiotic and a hormone.

6. The method according to claim 5, wherein the therapeutic agent comprises at least one of doxycycline and monocycline.

7. The method according to claim 5, wherein the therapeutic agent comprises insulin.

8. The method according to claim 1, wherein the therapeutic agent comprises at least one of a small organic molecule, a chemical compound, a peptide, a protein, a nucleic acid, a polysaccharide, and a lipid.

9. The method according to claim 8, wherein the therapeutic agent comprises at least one of isosorbide dinitrate, lignocaine, and selegiline.

10. The method according to claim 1, wherein the therapeutic agent comprises an anesthetic drug.

11. The method according to claim 1, wherein the plate further comprises a permeation enhancer for facilitating delivery of at least a therapeutic agent.

12. The method according to claim 11, wherein the permeation enhancer comprises at least one of bile salts, sodium glycocholate, sodium deoxycholate, sodium lauryl sulfate, sodium salicylate, sodium ethylenediaminetetraacetc acid, and aprotinin.

13. The method according to claim 1, wherein the plate further comprises a sustained time release mechanism for varying the rate of release of at least one of the therapeutic agent.

14. The method according to claim 13, wherein the sustained time release mechanism comprises a polymer microsphere.

15. The method according to claim 1, wherein the plate further comprises a liposome to enhance uptake of the therapeutic agent into cells.

16. The method according to claim 1, wherein the therapeutic agent is in solid form.

17. The method according to claim 1, wherein the therapeutic agent is in liquid form.

18. The method according to claim 1, wherein the therapeutic agent comprises particles capable of detaching from the U-shaped plate arid dissolving in a liquid.

19. The method according to claim 1, wherein biting comprises biting down on the plate to cover substantially the biting surface of the upper teeth and the lower teeth and to substantially block spaces between the upper teeth and the lower teeth.

20. The method according to claim 1, wherein rinsing comprises forcing the liquid through the crevices between adjacent teeth of the upper jaw and adjacent teeth of the lower jaw while the biting surfaces remain substantially covered by the plate.

21. The method according to claim 1, wherein the liquid is drawn into the mouth through a tube extending through the plate.

* * * * *